United States Patent [19]

Jones et al.

[11] Patent Number: 4,999,431
[45] Date of Patent: Mar. 12, 1991

[54] PROCESS FOR PREPARING QUINOLINE ALDEHYDE AND KETONE DERIVATIVES

[75] Inventors: Winton D. Jones; Richard C. Dage; George P. Claxton; Hsien C. Cheng, all of Cincinnati, Ohio; Phillip J. Robinson, Fitzroy, Australia

[73] Assignee: Merrell Dow Pharmaceuticals, Cincinnati, Ohio

[21] Appl. No.: 483,831

[22] Filed: Feb. 23, 1990

Related U.S. Application Data

[62] Division of Ser. No. 411,439, Sep. 22, 1989, abandoned, which is a division of Ser. No. 261,435, Oct. 24, 1988, Pat. No. 4,886,811.

[51] Int. Cl.$^5$ ............................................. C07D 215/14
[52] U.S. Cl. .................................................... 546/168
[58] Field of Search ......................................... 546/168

[56] References Cited

U.S. PATENT DOCUMENTS

| | | | |
|---|---|---|---|
| 1,145,487 | 7/1915 | Kaufmann | 546/168 |
| 2,798,071 | 7/1957 | Mathes et al. | 546/168 |
| 4,670,450 | 6/1987 | Schnettler et al. | 514/341 |
| 4,698,353 | 10/1987 | Schnettler et al. | 514/340 |
| 4,866,085 | 9/1989 | Schnettler et al. | 514/376 |

Primary Examiner—David B. Springer
Attorney, Agent, or Firm—William J. Stein

[57] ABSTRACT

This invention relates to novel quinolyloxazole-2-ones which are useful as protein kinase C inhibitors, effective in the treatment of hypertension and asthma. This invention also includes a novel procedure for producing an intermediate ketone compound involving the reaction of a bromo-quinoline compound with butyl lithium and further reacting the lithiated compound with N-methyl-N-methoxyalkanamide.

1 Claim, No Drawings

PROCESS FOR PREPARING QUINOLINE ALDEHYDE AND KETONE DERIVATIVES

This is a divisional of application Ser. No. 411,439, filed Sept. 22, 1989, now abandoned, which is a divisional of application Ser. No. 261,435, filed Oct. 24, 2988, now U.S. Pat. No. 4,886,811.

This invention relates to certain quinolyloxazole-2-ones of the formula

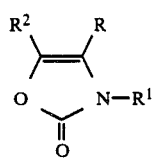

wherein
- R and $R^1$ are each independently selected from the group consisting of hydrogen, $C_1$-$C_6$ alkyl, and $C_1$-$C_3$ alkylphenyl wherein the phenyl ring is optionally substituted with one, two or three of the substituents selected from the group consisting of fluorine, chlorine, bromine, $C_1$-$C_4$ alkyl, and $C_1$-$C_4$ alkoxy; and
- $R^2$ is a 2-, 3-, or 4-quinolyl group wherein the quinolyl group is optionally substituted with one, two or three of the substituents selected from the group consisting of fluorine chlorine bromine, $C_1$-$C_4$ alkyl, $C_1$-$C_4$ alkoxy, nitro and trifluoromethyl; or $R^2$ is a 5-, 6-, 7-, or 8-quinolyl group;

and to the pharmaceutically-acceptable salts thereof.

This invention also concerns the use of the compounds of Formula I as protein kinase C inhibitors effective as vasodilators in the treatment of hypertension and as bronchodilators in the treatment of asthma. This invention also concerns a process for making certain intermediate ketone compounds which are useful in the synthesis of the compounds of Formula I.

As used herein, the terms "Cl-C3 alkyl", "$C_1$-$C_4$ alkyl" and "$C_1$-$C_6$ alkyl" mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propynyl, butenyl, butadienyl, isopropenyl, and the like. The term "$C_1$-$C_4$ alkoxy" means alkoxy groups having from one to four carbon atoms, and includes such groups as methoxy, ethoxy, n-propoxy, isopropoxy, n-butoxy, isobutoxy, sec-butoxy, tert-butoxy, and the like When R or $R^1$ is "optionally substituted $C_1$-$C_3$ alkylphenyl", the one, two or three substituent(s) can be located at any available position on the phenyl ring. When $R^2$ is 2-, 3-, or 4-quinolyl the optional substituent(s) can be located at any available position(s) on the quinolyl ring.

Illustrative examples of the compounds of this invention include compounds of Formula I wherein the R groups are designated as follows:

| R | $R^1$ | $R^2$ |
|---|---|---|
| hydrogen | hydrogen | 2-, 3-, or 4-quinolyl |
| ethyl | hydrogen | 2-, 3-, or 4-quinolyl |
| propyl | hydrogen | 5-, 6-, 7- or 8-quinolyl |
| methyl | benzyl | 2-, 3- or 4-quinolyl |
| phenethyl | hydrogen | 2-, 3- or 4-quinolyl |
| propyl | hydrogen | 2-, 3- or 4-(6,7-dimethyl)-quinolyl |
| 4-methoxyphenethyl | hydrogen | 2, 3- or 4-quinolyl |
| benzyl | benzyl | 2-, 3- or 4-(7-ethoxy)-quinolyl |
| butyl | hydrogen | 2-, 3- or 4-quinolyl |
| 3,5-dichloro)phenylpropyl | methyl | 5-, 6-, 7- or 8-quinolyl |
| propyl | methyl | 2-, 3- or 4-quinolyl |
| 3,5-dimethoxybenzyl | ethyl | 5-, 6-, 7- or 8 quinolyl |
| methyl | propyl | 2-, 3- or 4-(5-ethoxy-7-methyl)-quinolyl |
| butyl | butyl | 5-, 6-, 7- or 8-quinolyl |
| hydrogen | phenethyl | 2-, 3- or 4-(6-trifluoromethyl)-quinolyl |
| methyl | 4-methoxyphenethyl | 2-, 3- or 4-quinolyl |

As is true for most classes of therapeutically effective compounds, certain subclasses and certain species which are especially effective are preferred over others. In this instance, those compounds of Formula I wherein $R^2$ is optionally substituted 2-, 3-, or 4-quinolyl are preferred. Also preferred are compounds wherein r is $C_1$-$C_6$ alkyl, as well as compounds wherein $R^1$ is hydrogen. Most preferred are the compounds wherein $R^2$ is an unsubstituted 2-, 3-, or 4-quinolyl group, R is propyl and $R^1$ is hydrogen.

The 2-, 3-, or 4-quinolyloxazole-2-ones of this invention can readily be prepared by the reaction depicted in Reaction Scheme 1.

Reaction Scheme 1

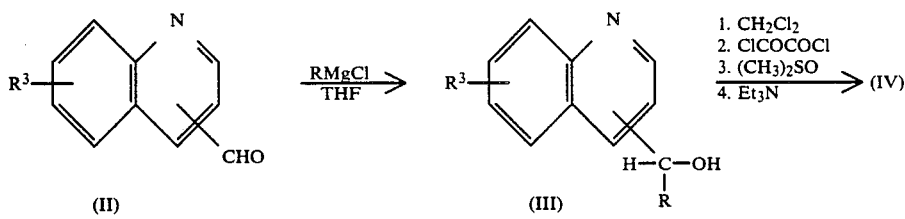

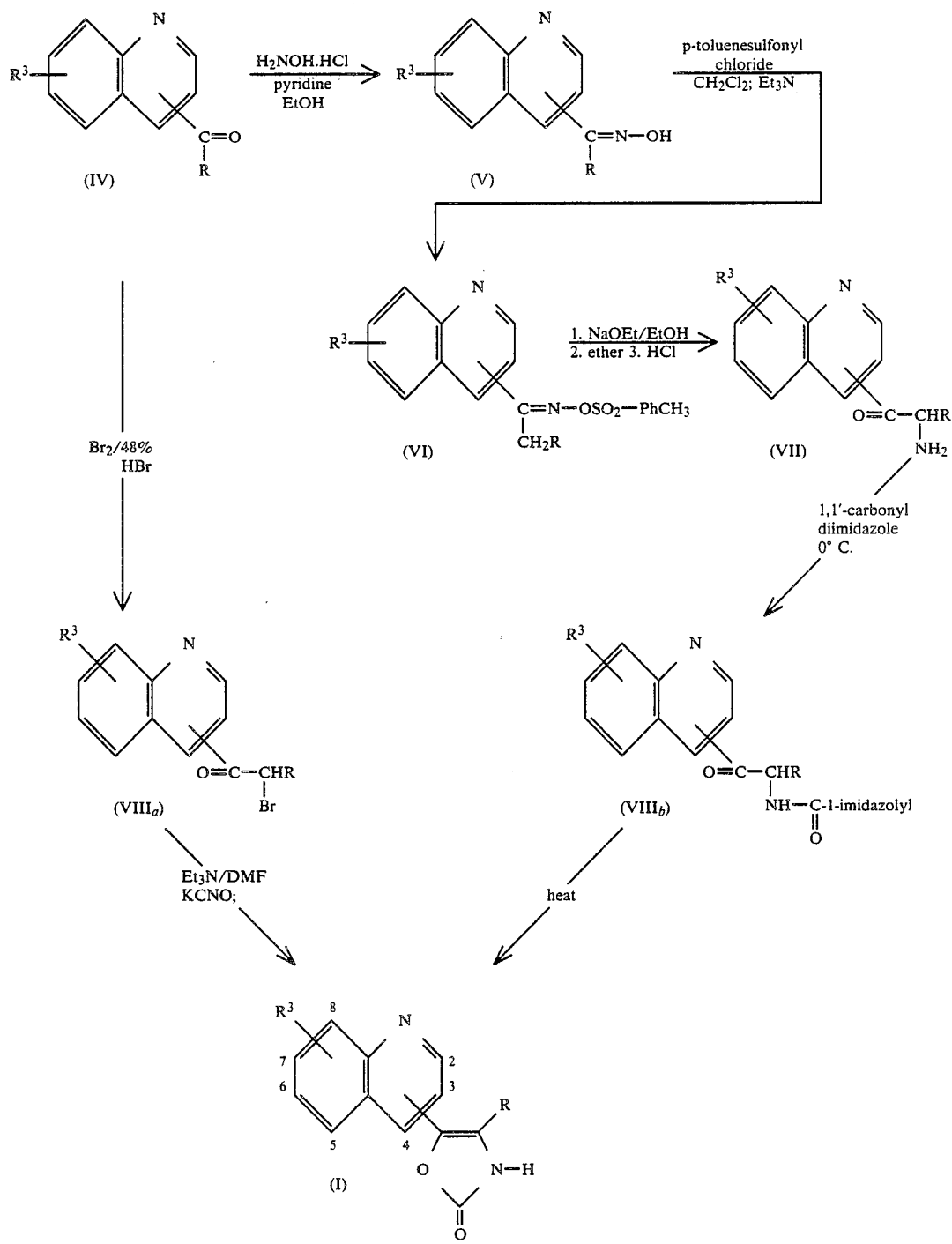

wherein R is as in Formula I, $R^3$ is the optional $R^2$ group substituent(s) of Formula I, and other symbols are as defined hereinafter.

In essence, Reaction Scheme 1 illustrates that the 2-, 3-, or 4-quinolyloxazole-2-ones of Formula I can be prepared by reacting the appropriate and readily available 2-, 3-, or 4-quinoline carboxaldehyde (II) in tetrahydrofuran (THF) with alkylmagnesium chloride or with optionally substituted phenylalkyl-magnesium chloride [RMgCl] to produce 2-, 3-, or 4-quinoline alkanol (III), which is in turn oxidized with oxalyl chloride (ClCOCOCl) methyl sulfoxide [(CH$_3$)$_2$SO] and triethylamine (Et$_3$N) in dichloromethane (CH$_2$Cl$_2$) to produce quinolyl-alkanone (IV). The alkanone (IV) can alternately be brominated to compound (VIII$_a$) and further treated with triethylamine in dimethylformamide (DMF) in the presence of potassium cyanate (KCNO) to form the compounds of Formula I according to procedures well known in the art and illustrated in the examples herein; or compound IV can be converted to oxime (V) by refluxing with hydroxylamine hydrochloride ($H_2NOH \cdot HCl$) and pyridine in ethanol (EtOH). Compound (V) is then reacted with p-toluenesulfonyl chloride and triethylamine in dichloromethane to produce compound (VI). The amine (VII) is then produced by reacting compound (VI) with sodium ethoxide in ethanol (NaOEt/EtOH), followed by ether and aqueous hydrochloric acid (HCl) extraction. The amine (VII) is further reacted with 1,1'-carbonyldiimidazole at about 0° C. to form compound (VIII$_b$), which is then heated to about 170° C. to yield the appropriate 2-, 3-, or 4-quinolyloxazole-2-ones of Formula I.

The unsubstituted 5-, 6-, 7- or 8-quinolyloxazole-2-ones of this invention can readily be prepared by the reaction depicted in Reaction Scheme 2.

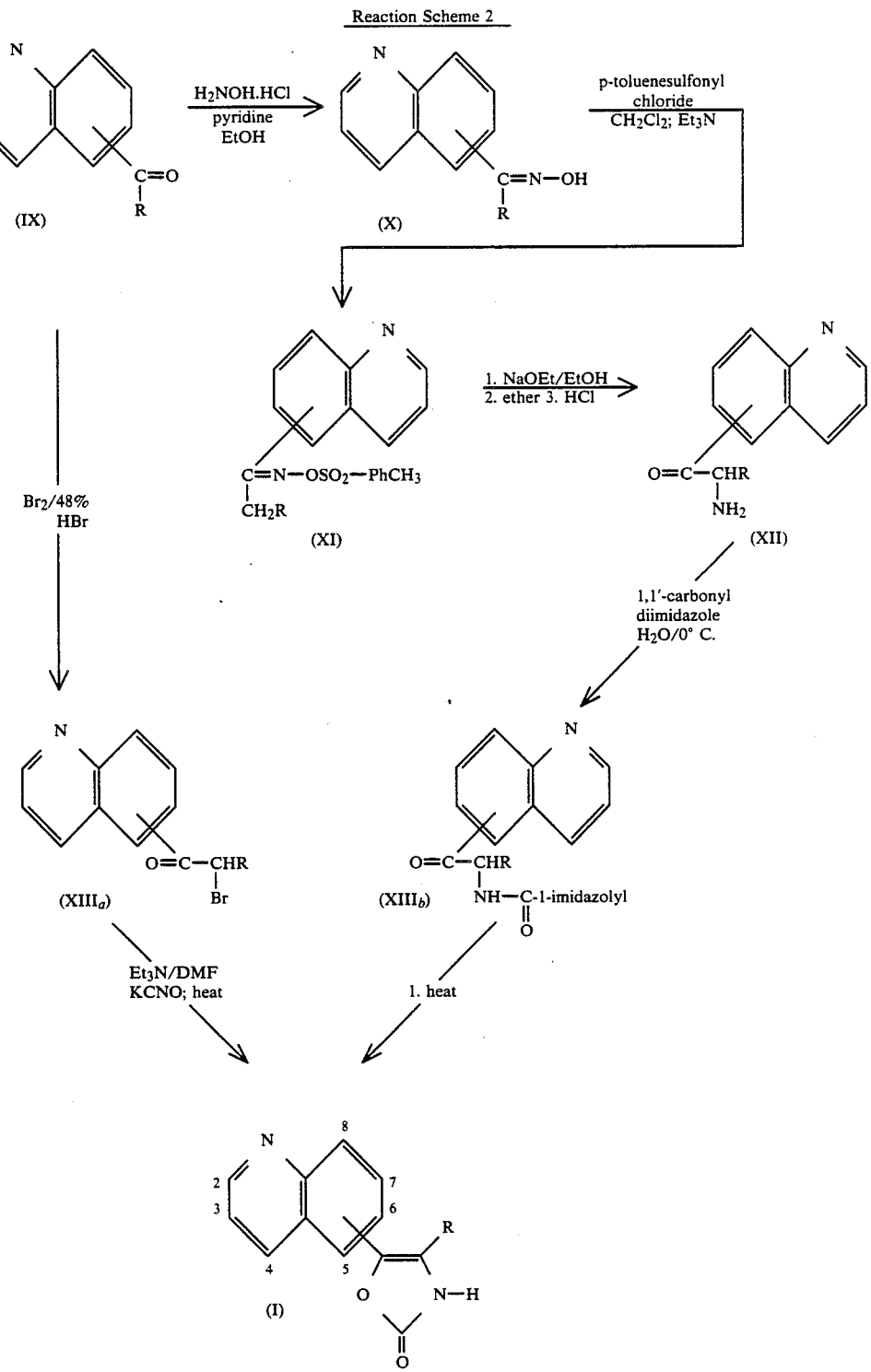

wherein R is as in Formula I, $R^3$ is the optional $R^2$ group substituent of Formula I, and other symbols are as defined for Reaction Scheme 1.

In essence, Reaction Scheme 2 illustrates that the 5-, 6-, 7-, or 8-quinolyloxazole-2-ones of Formula I can be prepared in essentially the same manner as described for Reaction Scheme 1. The alkanone starting material (IX) is prepared by metalating 5-, 6-, 7- or 8-bromoquinoline according to a procedure by H. Gilman and T. Suddy set forth in *J. Org. Chem.* 23, 1584-9 (1958), and then reacting it with N-alkoxy-N-alkylhydroxylamine. The 5-, 6-, 7-, or 8-bromoquinoline compounds are prepared by following procedures set forth in "The Chemistry of Heterocyclic Compounds" by Gurnos Jones, as found in Quinolines, Part 1, vol. 32, p. 100–117 and 247–258, ed. A Weissberger and E.C. Taylor, John Wiley and Sons, London, 1977. These procedures can also be utilized for preparing 2-,3-, or 4-bromoquinolines and their corresponding 2-, 3-, or 4- quinolinyl alkanones such as those of formula (IV) in Reaction Scheme 1.

Alternatively, the formula (IV) and formula (IX) compounds of Reaction Schemes 1 or 2 can also be prepared by reacting the appropriate bromoquinoline with butyl lithium in an appropriate solvent such as THF or ether at −70° C. to 0° C., preferably at −50° C., and then reacting the lithiated compound with

(XIV)

wherein R is as described in Formula I. This reaction is further specifically exemplified in Example 8 Compound (XIV) can be prepared by a procedure set forth in *Tetrahedron Letters*, 22, 3815 (1981).

The compounds wherein $R^1$ is $C_1$–$C_6$ alkyl or optionally substituted $C_1$–$C_3$ alkylphenyl are produced by subsequent reaction of the compound of Formula I of either Reaction Scheme 1 or Reaction Scheme 2 with sodium hydride and the appropriate alkyl iodide or phenylalkyl iodide in tetrahydrofuran according to procedures well known in the art.

The following specific examples are presented to illustrate the synthesis of the compounds of this invention, but they should not be construed as limiting the scope of this invention in any way.

EXAMPLE 1

1-Butyl-4-Quinoline Methanol (III)

In a 1 liter, 3-necked flask equipped with a mechanical stirrer, dropping funnel, reflux condenser (all dried under argon), and thermometer, were placed 15.0 grams (0.0954 M) of 4-quinoline carboxaldehyde and 400 ml of dry tetrahydrofuran (THF). The mixture was cooled by means of stirring in a dry ice/methanol bath to −70° C. Butylmagnesium chloride (100 ml of 2 M) was added through the funnel at a fast drop rate over a period of about 45 minutes, and the mixture was allowed to stir at −70° C. for about an hour. Then, 100 ml saturated ammonium chloride ($NH_4Cl$) was added dropwise through the funnel and the mixture was allowed to warm to room temperature whereupon the resulting semi-solid material was filtered off under vacuum and washed with about 100 ml THF. The THF layers were combined and washed with saturated sodium chloride solution and then dried over magnesium sulfate. The inorganic matter was filtered off by vacuum through diatomaceous earth and the solvent evaporated. The residue was flash chromatographed on silica (1:1 ethylacetate/hexane) and, after evaporation of the solvent, about 5.0 gram of purified title compound was recovered.

EXAMPLE 2

1-(4-Quinolinyl)-1 Pentanone (IV)

In a 1 liter, 3-necked flask equipped with a mechanical stirrer, dropping funnel, reflux condenser (all dried under argon), and thermometer, were placed 50 ml of dry dichloromethane and 3.79 ml (0.043 M) oxalyl chloride. The resulting mixture was stirred in a dry ice/methanol bath to maintain a temperature of −70° C. Methyl sulfoxide (6.17 ml, 0.043 M) was added dropwise and subsequently a solution of 9.26 grams (0.043 M) of the compound of Example 1 in dry dichloromethane ($CH_2Cl_2$) was added and the mixture allowed to stir cold for about 15 minutes. Triethylamine (35.6 ml) was then added and the mixture was allowed to stir cold for about 1 hour. After the mixture had been allowed to warm to room temperature, it was poured into a flask containing about 600 ml water. The $CH_2Cl_2$ layer was separated and the aqueous layer extracted with $CH_2Cl_2$ (2 times, 100 ml each). The combined $CH_2Cl_2$ layers were washed with saturated sodium chloride and dried over magnesium sulfate. The inorganic matter was filtered off and the solvent evaporated leaving a residue that was flash chromatographed as in Example 1. Evaporation left 9.0 grams of title compound.

EXAMPLE 3

1-(4-Quinolinyl) 1-Pentanone Oxime (V)

In a 500 ml, 3-necked flask equipped with a mechanical stirrer, dropping funnel, reflux condenser (all dried under argon), were placed 8.3 grams (0.03892 M) of the compound of Example 2, 4.12 grams (0.0584 M) of hydroxylamine hydrochloride, 40 ml of dry pyridine, and about 200 ml of dry ethanol The mixture was refluxed for 6 hours, then the solvent was evaporated leaving a residue which was treated with about 400 ml ether and 200 ml water. The ether layer was separated and washed several times with water, washed with saturated sodium chloride and dried over magnesium sulfate. The inorganic matter was filtered off and the solvent evaporated, leaving 8.42 grams (94.7%) of the title compound.

EXAMPLE 4

1 (4 Quinolinyl)-1-Pentanone 0 [(4 Methylphenyl)Sulfonyl]

Oxime (VI)

In a 250 ml erhlenmeyer flask filled with argon were placed 8.42 grams (0.0369 M) of the compound of Example 3 and about 130 ml dry $CH_2Cl_2$. While stirring and cooling to about 0° C. in an ice/methanol bath, about 20 ml of triethylamine was added over a 5 minute period, then 10.55 grams (0.0554 M) toluenesulfonyl chloride was added and the mixture allowed to stir for 3 hours. The solution was then evaporated to dryness which left a residue that was treated with ether and water. The ether phase was separated and the water phase extracted twice more with ether. The combined ether layers were extracted with dilute sodium hydroxide, washed with saturated sodium chloride and dried over magnesium sulfate. The inorganic matter was filtered off using vacuum, and the solvent was evaporated leaving 15.1 grams of the title compound.

EXAMPLE 5

2 Amino 1-(4 Quinolinyl)-1 Pentanone (VII)

In a 250 ml, 3-necked flask equipped with a mechanical stirrer, dropping funnel, reflux condenser (all dried under argon), was placed 60 ml dry ethanol. While stirring, 2.55 grams (0.111 M) of sodium spheres were added and allowed to continue to stir under argon until the sodium dissolved. A solution of 15.1 grams of the compound of Example 4 in ethanol was then added and the mixture stirred for 4 hours at room temperature. The mixture was then poured into a flask containing 1200 ml absolute ether. The resulting precipitate was filtered off under vacuum through diatomaceous earth, and the filtrate extracted with 2N hydrochloric acid (3 times, 170 ml each). The extract was evaporated leaving 19.8 grams of the title compound.

EXAMPLE 6

N-[2-Oxo-1-Propyl 2 (4-Quinolinyl)Ethyl] 1H-Imidazole-1 -Carboxamide (VIII$_b$)

The compound of Example 5 (19.8 grams) was dissolved in about 300 ml water, and the solution filtered by gravity into a 1 liter, 3-necked flask equipped with a mechanical stirrer and a thermometer. The solution was o cooled to 0° C. with stirring in an ice/methanol bath, and 29.87 grams (0.185 M) 1,1'-carbonyldiimidazole was added over a 5 minute period. The mixture was allowed to stir cold for about 15 minutes The resulting precipitate was taken up in about 500 ml ethyl acetate and separated from the water. The solution was washed with saturated sodium chloride and dried over magnesium sulfate, and the inorganic matter filtered off using diatomaceous earth under vacuum. The solvent was evaporated leaving the title compound.

EXAMPLE 7

4-Propyl 5-(4-Quinolinyl)-2-(3H)-Oxazolone (I)

The compound of Example 6 (12 grams) was heated under vacuum to 170° C. for about 30 minutes, allowed to cool to room temperature and washed with water. The water was decanted and the residue was treated with $CH_2Cl_2$ (20 ml). The $CH_2Cl_2$ was evaporated leaving 7.8 grams of residue The product was purified by means of flash chromatography on silica, eluting with ethylacetate. The solvent was evaporated and the residue dissolved in 48 ml hot 50% ethanol, filtered and allowed to cool to room temperature. The precipitate was collected by vacuum filtration and dried in vacuo at 78° C., leaving 1.97 grams (21%) title compound.

M.p. 188–190° C. dec.; analysis calced. for $C_{15}H_{14}N_2O_2$: C, 70.85; H, 5.55; N, 11.02; analysis found C, 71.10; H, 5.73; N, 10.76.

EXAMPLE 8

1-(3 Quinolinyl) 1 butanone

In a dry 3-necked flask under argon at −50° C., n-butyl lithium (0.0025 M, 0.021 ml) was added to 150 ml diethylether. Then 4.16 grams 3-bromoquinoline in 2 ml THF was added dropwise while stirring and maintaining the temperature at −60° C. to −55° C. The solution was stirred for 30 minutes, and 2.3 grams N-methyl-N-methoxybutanamide were then added dropwise at −50°

C. and the solution was stirred an additional 30 minutes The solution was then allowed to warm to 0° C. and stirred for one hour. The reaction was quenched with a saturated solution of ammonium chloride and the THF layer separated, washed with brine, separated, and dried over magnesium sulfate. Filtration through diatomaceous earth, followed by concentration and subsequent thin layer chromatography (35% ethylacetate/65% $CH_2Cl_2$) gave a total yield of 2.03 g (51%) of the title compound.

By substituting the following starting materials for the 4-quinoline carboxaldehyde and/or the butylmagnesium chloride of Example 1, and following the procedures set forth in Examples 1 through 7, the following end products can be made in a like manner.

A. 6- or 8-methoxy-4-quinoline carboxaldehyde and methylmagnesium chloride, to yield 5-(6- or 8-methoxy4-quinolinyl)-2-(3H)-oxazolone B. 2-quinololine carboxaldehyde and methylmagnesium
 chloride, to yield 5-(2-quinolinyl)-2-(3H)-oxazolone C. 7- or 8-chloro-4-quinoline carboxaldehyde and propylmagnesium chloride, to yield 4-ethyl-5-(7- or 8-chloro-4-quinolinyl)-2-(3H)-oxazolone D. 6,8-dichloro or dibromo-4-quinoline carboxaldehyde and
butylmagnesium chloride, to yield 4-propyl-5-(6,8-dichloro or dibromo-4-quinolinyl)-2-(3H)-oxazolone E. 7- or 8-nitro-4-quinoline carboxaldehyde and pentylmagnesium chloride, to yield 4-butyl-5-(7- or 8-nitro-4-quinolinyl)-2-(3H)-oxazolone F. 7-trifluoromethyl-4-quinoline carboxaldehyde and hexylmagnesium chloride, to yield 4-pentyl-5-(7-trifluoromethyl-4-quinolinyl)-2-(3H)-oxazolone G. 5,8 dimethoxy-4-quinoline carboxaldehyde and benzylmagnesium chloride, to yield 4-phenyl-5-(5,8-dimethoxy-4-quinolinyl)-2-(3H)-oxazolone H 5,8-dimethoxy-6-nitro-4-quinoline carboxaldehyde and ethylmagnesium chloride, to yield 4-methyl-5-(5,8-dimethoxy-6-nitro-4-quinolinyl)-2-(3H)-oxazolone I. 6-methoxy-8-nitro-4-quinoline carboxaldehyde and propylmagnesium chloride, to yield 4-ethyl-5-(6-methoxy-8-nitro-4-quinolinyl)-2-(3H)-oxazolone J. 5,6-dimethoxy-8-nitro-4-quinoline carboxaldehyde and pentylmagnesium chloride, to yield 4-butyl-5-(5,6-dimethoxy-8-nitro-4-quinolinyl)-2-(3H)-oxazolone K. 5-methyl-4-quinoline carboxaldehyde and benzylmagnesium chloride, to yield 4-phenyl-5-(5-methyl-4-quinolinyl)-2-(3H)-oxazolone L. 2-(4-methoxy)phenyl-4-quinoline carboxaldehyde and 3,5-dimethoxybenzymagnesium chloride, to yield 4-(3,5-dimethoxyphenyl)-5-[1-(4-methoxyphenyl)-4-qui nolinyl]-2-(3H)-oxazolone By substituting 1-(3-quinolinyl)-1-pentanone for the M. 6,8-dimethoxy-4-quinoline carboxaldehyde and 4-methylbenzylmagnesium chloride, to yield 4-(4-methylphenyl)-5-(6,8-dimethoxy-4-quinolinyl)-2-(3H)-oxazolone By substituting 1-(3-quinolinyl)-1-pentanone for the compound of Example 2 and by following the procedure set forth in Examples 3 through 7, 4-propyl-5-(3-quinolinyl)-2-(3H)-oxazolone is produced.

In a like manner, by substituting the following starting materials for 1-(4-quinolinyl)-1-pentanone of Example 2 and following the procedure set forth in the preceding paragraph, the following end products can be made.

N. 1-(5-quinolinyl)-1-pentanone, to yield 4-propyl-5-(5-quinolinyl)-2-(3H)-oxazolone
O. 1-(6-quinolinyl)-1-butanone, to yield 4-ethyl-5-(6-quinolinyl)-2 (3H)-oxazolone
P. 1-(7-quinolinyl)-1-ethanone, to yield 5-(7-quinolinyl)-2-(3H)-oxazolone
Q. 1-(8-quinolinyl)-1-phenylethanone, to yield 4-phenyl5-(8-quinolinyl)-2-(3H)-oxazolone
R. 1-(5,8-dimethoxy-3-quinolinyl)-1-propanone, to yield 4-methyl-5-(5,8-dimethoxy-3-quinolinyl)-1-(3H)-oxazolone The compounds of this invention are useful both in the free base form and as salts. The expression "pharmaceutically-acceptable salt" means any organic or inorganic addition salt of the base compounds of Formula I which are relatively non-toxic and innocuous to a patient at concentrations consistent with effective activity so that the side effects ascribable to the salt do not vitiate the beneficial effects of the base compounds of Formula I. These salts are included within the scope of this invention. Such salts include alkali metal salts, such as sodium and potassium salts and alkaline earth metal salts, such as calcium and magnesium salts; and the like. Also salts with organic and inorganic acids can be prepared, such as, for example, those formed with the following acids: hydrochloric, hydrobromic, sulfonic, sulfuric, phosphoric, nitric, ascorbic, methanesulfonic, acetic, propionic, tartaric, citric, lactic, malic, mandelic, cinnamic, palmitic, itaconic, fumaric, benzenesulfonic and toluenesulfonic. The non-toxic, physiologically acceptable salts are preferred, although other salts are also useful, for example, in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

The compounds of Formula I are antihypertensive agents, useful for lowering blood pressure. The utility of the compounds of Formula I as antihypertensive agents may be determined by a procedure wherein male, spontaneously-hypertensive rats are monitored for blood pressure changes by means of a tail-cuff technique described by R. C. Dage, et al in *J. Cardiovasc. Pharmacol.*, 3, 299-315, 1981. Blood pressure lowering in spontaneously hypertensive rats over time, effectuated by a 50 milligram per kilogram (mg/kg) interperitoneally administered dose of a compound of Formula I, is presented in Table I below.

tive ingredient (i.e., a compound of Formula I) to be administered to a patient for the treatment of hypertension can vary widely according to such considerations as the particular compound and dosage unit employed, the period of treatment, the age and sex of the patient treated, and the extent of the hypertension treated.

The total amount of active ingredient to be administered intravenously will generally range from about 0.1 mg/kg to 30 mg/kg and preferably from 1.0 mg/kg to 10.0 mg/kg. A unit dosage may contain from 5 mg to 525 mg of active ingredient, and can be taken one or more times per day. For example, a 50 kg patient may be administered 50 mg-700 mg active ingredient four times a day for a total dose of 200 mg-2800 mg per day.

The total amount of active ingredient to be administered orally will generally range from 0.1 mg/kg to 100 mg/kg, and preferably from 1.0 mg/kg to 50 mg/kg. A unit dosage may contain from 5 mg to 1000 mg of active ingredient, and can be taken one or more times per day. For example, a 50 kg patient may be administered 50 mg- 2500 mg of active ingredient four times a day for total of 200 mg-10,000 mg per day.

The compounds of this invention can be administered as the sole anti-hypertensive agent or in combination with other anti-hypertensive agents and/or diuretic agents and/or calcium entry blocking agents. For example, the compounds of this invention can be given in combination with such compounds as benzthiazide, clonidine, deserpidine, furosemide, hydralazine hydrochloride, indacrinone and variable ratios of its enantiomers, prazosin, propranolol, reserpine, and the like, as well as admixtures and combinations thereof.

Typically, the individual daily dosages for these combinations can range from about one fifth of the minimally recommended clinical dosages to the maximum recommended levels for the entities when they are given singly.

When the compounds of this invention are administered as a bronchodilatory agents in the treatment of, for example, asthma, the amount of active ingredient to be administered can vary widely according to such considerations as the particular compound and dosage unit employed, the period of treatment, the age and sex of the patient treated, and the extent of the condition treated. The total amount of active ingredient to be administered parenterally or by inhalation will generally range from about 0.1 mg/kg to 30.0 mg/kg and preferably from 1 mg/kg to 10 mg/kg. A unit dosage may contain from 5 mg to 525 mg of active ingredient, and can be taken one or more times per day. For example, a 50 kg patient may be administered 50 mg to 700 mg active ingredient, four times a day for a total dose of 200 mg-2800 mg per day.

The compounds of this invention can be utilized to achieve the desired pharmacological effect by administration to a patient in need thereof in an appropriately formulated pharmaceutical composition. Therefore, the

TABLE I

| Test Compound | Blood Pressure (mm Hg) Change From Control At Time After Treatment | | | | |
|---|---|---|---|---|---|
| | Control | Change in Blood Pressure | | | |
| | | 1 hr. | 2 hr. | 3 hr. | 4 hr. |
| Carrier | 201+/−3 | −8+/−4 | −2+/−6 | −6+/−6 | −10+/−5 |
| 1 | 209+/−7 | −6+/−9 | *−24+/−7 | *−26+/−4 | −25+/−6 |

Compound 1: 4-propyl-5-(4-quinolinyl)-2(3H)-oxazolone
*significant effect $p < 0.05$ A patient, for the purpose of this invention, is a mammal, including a human, in need of treatment for a particular condition, injury or disease. The amount of acpresent invention includes pharmaceutical compositions which are comprised of a pharmaceutically-acceptable carrier and a pharmaceutically-effective amount of a compound of Formula I. A pharmaceutically-acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically-effective amount of compound is that amount which produces a result or exerts an influence on the particular condition being treated. The compounds of Formula I can be administered with a pharmaceutically acceptable carrier using conventional dosage unit forms orally, parenterally, topically, as an aerosol, or the like.

For oral administration the compounds can be formulated into solid or liquid preparations such as capsules, pills, tablets, troches, lozenges, melts, powders, solutions, suspensions, or emulsions and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of this invention may be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxy cetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil such as, for example, arachis oil, olive oil, sesame oil or coconut oil, or in a mineral oil such as liquid paraffin The oily suspensions may contain a thickening agent such as, for example, beeswax, hard paraffin or cetyl alcohol. The sterile injectable preparation may also be a sterile injectable solution or suspension in a non-toxic parenterally-acceptable diluent or solvent. Diluents and solvents that may be employed are, for example, water, Ringer's solution, and isotonic sodium chloride solution In addition, sterile fixed oils are conventionally employed as solvents or suspending media. For this purpose, any bland, fixed oil may be employed including synthetic monoor diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The compounds of this invention may be formulated as solutions, suspensions, emulsions, powders, and semisolid preparations administered as an aerosol preparation by means of a pressurized aerosol container together with a gaseous or liquefied propellant such as, for example, dichlorodifluoromethane, dichlorodifluoromethane with dichlorodifluoroethane, carbon dioxide, nitrogen, propane, or the like, with the usual adjuvants such as co-solvents and wetting agents, as may be necessary or desirable. The form such as in a nebulizer or atomizer. The aerosols are intended for administration as fine, solid particles or as liquid mists via the respiratory system, and the particle size of aerosol preparations intended for administration to the lungs should be below 50 micrometers, in most instances.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

The compositions of the invention can also contain other conventional pharmaceutically-acceptable compounding ingredients, generally referred to as carriers or diluents, as necessary or desired. Any of the compositions of this invention may be preserved by the addition of an antioxidant such as ascorbic acid or by other suitable preservatives Conventional procedures for preparing such compositions in appropriate dosage forms can be utilized.

The following specific examples are presented to illustrate compositions of this invention, but they should not be construed as limiting the scope of this invention in any way.

EXAMPLE 9

| | |
|---|---|
| A tablet is prepared from 4-Methyl-5-(3-quinolinyl)-2-(3H)-oxazolone | 250 mg |
| Starch | 40 mg |
| Talc | 10 mg |
| Magnesium | 10 mg |

EXAMPLE 10

A capsule is prepared from 4-phenyl-5-(2-quinolinyl)

| | |
|---|---|
| A capsule is prepared from 4-phenyl-5-(2-quinolinyl)-2-(3H)-oxazolone | 400 mg |
| Talc | 40 mg |
| Sodium Carboxymethyl cellulose | 40 mg |
| Starch | 120 mg |

The compounds of Formula I may also be utilized, in free base form or in compositions, in research and diagnostics, or as analytical references or standards, and the like. Therefore, the present invention includes compositions which are comprised of an inert carrier and an effective amount of a compound of Formula I, or a salt thereof. An inert carrier is any material which does not interreact with the compound to be carried and which lends support, means of conveyance bulk, traceable material, and the like to the compound to be carried. An effective amount of compound is that amount which produces a result or exerts an influence on the particular procedure being performed.

It should be apparent to one of ordinary skill in the art that changes and modifications can be made to this invention without departing from the spirit or scope of the invention as it is set forth herein.

What is claimed as new and useful is:

1. A process for preparing a compound of the formula

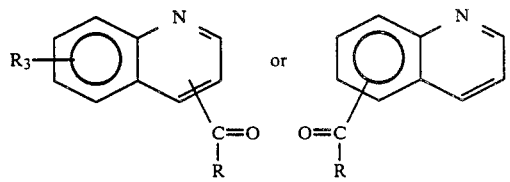

wherein
R is hydrogen, $C_1$-$C_6$ alkyl and $c_1$-$C_3$ alkylphenyl wherein the phenyl ring is optionally substituted with one, two or three of the substitutents selected from the group consisting of fluorine, chlorine, bromine, $C_1$-$C_4$ alkyl, and $C_1$-$C_4$ alkoxy nitro and trifluoromethyl; and $R_3$ is an optional substitutent selected from the group consisting of fluorine, chlorine, bromine, $C_1$-$C_4$ alkyl, $C_1$-$C_4$ alkoxy, nitro, and trifluoromethyl, which comprises reacting a 2-, 3-, 4-, or a 5-, 6-, 7- or 8-bromoquinoline with butyl lithium in a solvent at a temperature of from $-70°$ C. to $0°$ C., and then further reacting the lithiated compound with a compound of the formula
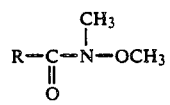
* * * * *